(12) United States Patent
Brosnahan et al.

(10) Patent No.: US 6,607,557 B1
(45) Date of Patent: Aug. 19, 2003

(54) ARTIFICIAL BONE GRAFT IMPLANT

(75) Inventors: Robert Brosnahan, Germantown, TN (US); Laura A. Small, Memphis, TN (US); Julie A. Bearcroft, Bartlett, TN (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/718,968

(22) Filed: Nov. 22, 2000

Related U.S. Application Data

(62) Division of application No. 08/940,660, filed on Sep. 29, 1997, now Pat. No. 6,149,688, which is a continuation of application No. 08/473,658, filed on Jun. 7, 1995, now abandoned.

(51) Int. Cl.[7] .................................................. A61F 2/44
(52) U.S. Cl. .................................. 623/17.11; 623/23.51; 623/23.76; 623/23.56
(58) Field of Search ............................. 623/23.5, 23.51, 623/23.56, 23.76, 23.57, 23.75, 17.11, 17.16; 606/76

(56) References Cited

U.S. PATENT DOCUMENTS

| | | | | |
|---|---|---|---|---|
| 3,867,728 A | * | 2/1975 | Stubstad et al. | 623/17.16 |
| 4,164,794 A | * | 8/1979 | Spector et al. | 427/195 |
| 4,351,069 A | * | 9/1982 | Ballintyn et al. | 623/23.36 |
| 4,542,539 A | * | 9/1985 | Rowe et al. | 623/23.57 |

(List continued on next page.)

FOREIGN PATENT DOCUMENTS

| | | |
|---|---|---|
| EP | 0 577 342 A1 | 5/1994 |
| EP | 0 599 419 | 6/1994 |
| WO | WO 94/10100 | 5/1994 |

OTHER PUBLICATIONS

Koji Ioku et al., Dense/Porous Layered Apatite Ceramics Prepared by HIP, vol. 8, No. 10 Oct. 1989, JMTSAS 8(10) 1117–1240 (1989) ISSN 0261 8028 Chapman and Hall.

S. Best et al., Processing Behaviour of Hydroxyapatite Powders with Contrasting Morphology, Journal of Materials Science: Materials in Medicine 5 (1994) 516–521.

Pauchiu E. Wang et al., Sintering Behaviour and Mechanical Properties of Hydroxyapatite and Dicalcium Phosphate; Journal of Materials Science: Materials in Medicine 4 (1993) 150–158.

M. Jarcho et al., Hydroxylapatite Synthesis and Characterization in Dense Polycrystalline Form, Journal of Materials Science II (1976), 2027–2035.

*Primary Examiner*—Paul B. Prebilic
(74) *Attorney, Agent, or Firm*—Lerner, David, Littenberg, Krumholz & Mentlik, LLP

(57) ABSTRACT

An implant for replacing the supporting function of an intervertebral space defined between adjacent vertebrae includes a prosthetic implant member dimensioned for insertion within a space provided by at least partial removal of the intervertebral disc. The implant member includes a first implant portion and a second implant portion. The first implant portion includes a microporous material formed to define a predetermined configuration and has a first relatively high average porosity to facilitate rapid bone ingrowth within the first implant portion. The second implant portion includes a microporous material formed to define a predetermined configuration and has a second relatively low average porosity to support and maintain the adjacent vertebrae in spaced relation during permanent fixation of the implant member within the adjacent vertebrae. The first implant portion is disposed in a peripheral area of the implant member and the second implant portion is disposed in a central area of the implant member such that the first implant portion substantially encapsulates the second implant portion.

8 Claims, 3 Drawing Sheets

U.S. PATENT DOCUMENTS

| | | |
|---|---|---|
| 4,629,464 A | 12/1986 | Takata et al. |
| 4,756,862 A * | 7/1988 | Spector et al. .............. 264/126 |
| 4,863,472 A | 9/1989 | Tormala et al. |
| 5,152,791 A | 10/1992 | Hakamatsuka et al. |
| 5,258,043 A | 11/1993 | Stone |
| 5,279,831 A | 1/1994 | Constantz et al. |
| 5,306,307 A | 4/1994 | Senter et al. |
| 5,306,308 A | 4/1994 | Gross et al. |
| 5,306,309 A | 4/1994 | Wagner et al. |
| 5,769,897 A | 6/1998 | Harle |
| 6,149,688 A * | 11/2000 | Brosnahan et al. ........ 623/23.5 |

* cited by examiner

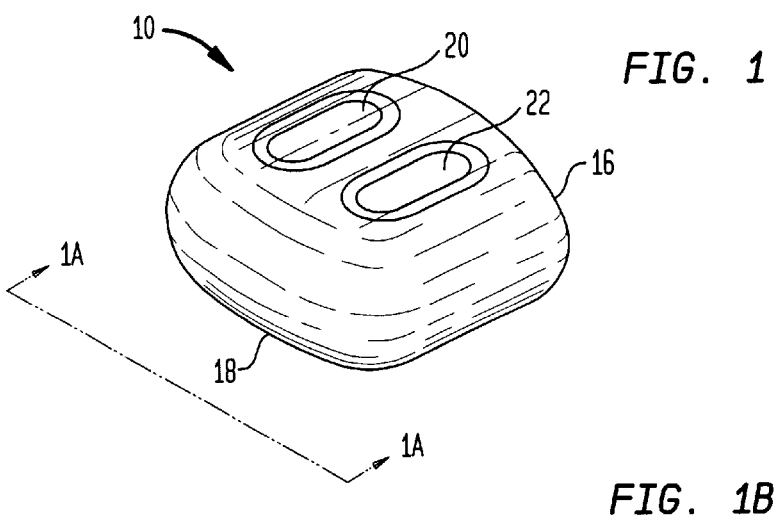
FIG. 1
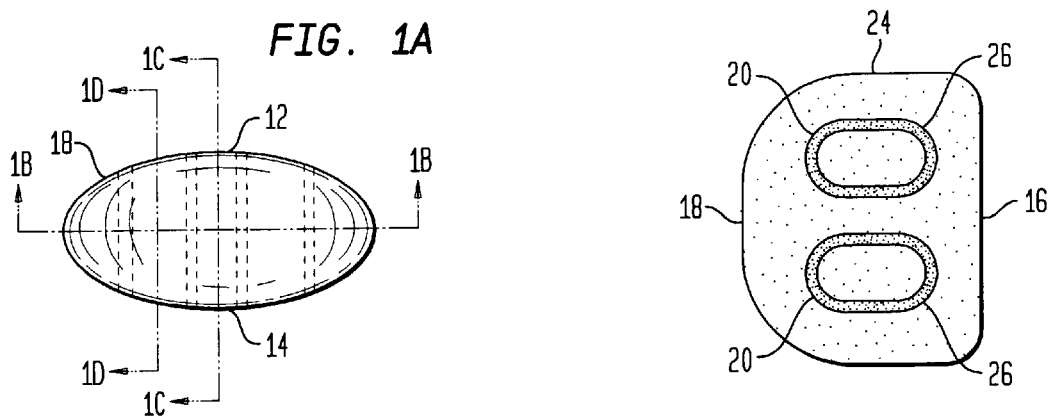
FIG. 1A
FIG. 1B
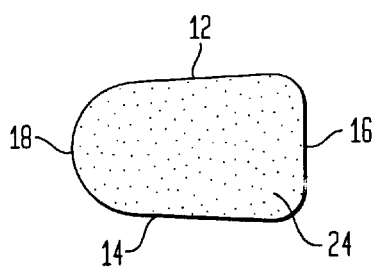
FIG. 1C
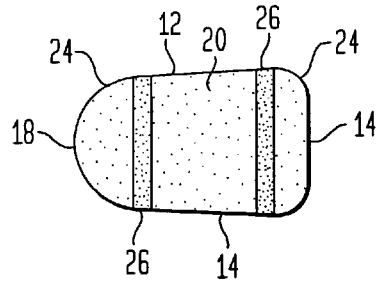
FIG. 1D

ARTIFICIAL BONE GRAFT IMPLANT

The present application is a divisional of U.S. patent application Ser. No. 08/904,660 filed Sep. 29, 1997, now U.S. Pat. No. 6,149,688, which is a continuation of U.S. patent application Ser. No. 08/473,658 filed Jun. 7, 1995, now abandoned. The disclosures set forth in the '660 and '658 applications are hereby incorporated by reference herein.

FIELD OF THE INVENTION

The present invention relates to artificial bone graph implants and more specifically to artificial bone graft implants constructed so as to allow bone ingrowth while maintaining a load-bearing strength similar to natural bone.

BACKGROUND OF THE INVENTION

There are numerous surgical situations in which bone grafts are used as part of the surgical procedure. For example, bone grafts are used in facial reconstruction, in repairing long bone defects, and in spinal surgery such as intervertebral discectomy and fusion in which a bone graft implant replaces a spinal disc in the intervertebral space.

Bone used for bone graft implants is often removed from another portion of a patient's body, which is called an autograft. A significant advantage of using a patient's own bone is the avoidance of tissue rejection, but harvesting bone also has its shortcomings. There is a risk to the patient in having a second surgical procedure (bone harvesting) performed at a secondary site which can lead to infection or additional pain to the patient. Further, the bone harvesting site is weakened by the removal of the bone. Also, the bone graft implant may not be perfectly shaped which can cause misplacement of the implant. This can lead to slippage or absorption of the implant, or failure of the implant to fuse with the bone it is in contact with.

Other options for a bone graft source is bone removed from cadavers, called allograft, or from an animal, called xenograft. While these kinds of bone grafts relieve the patient of having a secondary surgical site as a possible source of infection or pain, this option carries a high incidence of graft rejection and an increased risk of the transmission of communicable diseases.

An alternative to using living bone graft implants is the use of a manufactured implant made of a synthetic material that is biologically compatible with the body. With varying success, several synthetic compositions and various geometries of such implants have been utilized. In some instances, the implanting surgery of such implants is accomplished without difficulty, but the results can be unsatisfactory because any minor dents or imperfections in the implant can cause poor bone-to-implant bonding or an implant having a very high porosity can collapse due to lack of mechanical strength. In other instances, the artificial implant requires a complex surgical procedure that is difficult to perform and may not lead to correction of the problem again, because of the above discussed side effects or dislocation of the artificial implant. Presently, no fully satisfactory artificial implant is known that can be implanted with a relatively straightforward procedure.

Considerable study has been devoted to the development of materials that can be used for medical implants, including load-bearing implants, while allowing ingrowth of new bone tissue into the implant. To be suitable for this use, the material must meet several criteria, namely biocompatibility, porosity which allows tissue ingrowth and a mechanical strength suitable to bearing loads expected of natural bone without greatly exceed the natural bone's stiffness.

Several materials have been examined as potential implant materials including ceramics, such as hydroxylapatite, $Ca_{10}(PO_4)_6(OH)_2$, hardened polymers and biocompatible metals. Hydroxylapatite (HAp) has been of particular interest because of its similarity to natural bone mineral, but it has only been used for low load bearing applications as pure porous HAp itself is relatively low in mechanical strength and may not serve as a good prosthetic material for high load bearing implants.

Studies have been directed at improving the mechanical strength properties of an HAp material in order to render it suitable as a high load bearing prosthetic material. European patent EP 0577342A1 to Bonfield et al. discloses a sintered composite of HAp and a biocompatible glass based on CaO and $P_2O_5$ that may be used in dental and medical applications as a replacement for unmodified HAp. To date, improvements in the mechanical strength of HAp material has been achieved at the expense of its porosity. Upon densification necessary to achieve adequate load bearing strength, the HAp material has a porosity which is insufficient to provide the desired degree of bone ingrowth.

In a study entitled "Dense/porous Layered Apatite Ceramics Prepared by HIP Post Sintering," *Materials Science*, Vol. 8, No. 10, pp 1203 (October, 1989), by Ioku et al., the preparation of layers of dense HAp and porous HAp from two different types of HAp powder is discussed. This structure is prepared by first densifying specially produced fine crystals of HAp with a post-sintering process employing hot isostatic pressing (HIP). Then a commercial, coarse HAp powder is molded in layers with the densified HAp. Despite its being of academic interest, this type of HAp structure is not suitable for fabrication into load bearing bone prosthetic device configurations in which natural bone ingrowth may be achieved because of its lack of strength. However, Ioku suggests that the addition of zirconia whiskers into the dense HAp layer might provide some of the toughness necessary for hard-tissue prosthetic applications.

Still desired in the art is an artificial bone graft implant that is formed of a biocompatible mineral material similar to bone which possesses compressive strength close to that of natural bone while providing for ingrowth of bone tissue for permanent fixation.

SUMMARY OF THE INVENTION

The present invention provides an artificial bone graft implant formed of a biocompatible mineral material which possesses compressive strength similar to that of natural bone and allows bone tissue ingrowth for permanent fixations. The artificial bone graft implant is used as a replacement for living bone material in surgical procedures requiring the use of bone graft material. The inventive implant has a body configured to be implanted into a prepared site in a patient's bone tissue, with the body having a pair of opposed outer surfaces defining the body. A first and a second porous portion form the body with the first and second porous portions having pores of different sizes such that the average pore size of the first porous portion is greater than the average pore size of the second porous portion. The first porous portion of the body is formed in the shape of a core, with the core being in contact with the opposed outer surfaces of the body, and the second porous portion of the body is formed in the shape of an outer shell. The pore size of the first porous portion of the implant allows for the ingrowth of bone tissue while the pore size of the second portion of the implant allows for a load bearing capacity similar to natural bone.

As will subsequently be described, the unique hybrid structure of a dense outer shell and a porous core provides load bearing support while simultaneously allowing bone ingrowth. The implant of the invention may be readily implanted by established surgical procedures, with minimal need to alter known surgical procedures. The hybrid porous/dense construction of the implant ensures normal load bearing and support through the eventual ingrowth of bone tissue, and minimizes the likelihood of implant dislocation relative to adjacent bone tissue either during surgery or during the post-operative fusion process.

BRIEF DESCRIPTION OF THE DRAWINGS

A better understanding of the invention can be obtained when the detailed description of exemplary embodiments set forth below is reviewed in conjunction with the accompanying drawings, in which:

FIG. 1 is a perspective view of the present invention in the form of a spinal disc implant;

FIG. 1A is a plan view of the posterior end of the implant of FIG. 1 taken along lines 1A—1A;

FIG. 1B is a cross-sectional view of the implant of FIG. 1 taken along the lines 1B—1B in FIG. 1A;

FIG. 1C is a cross sectional view of the implant of FIG. 1 taken along lines 1C—1C in FIG. 1;

FIG. 1D is a cross-sectional view of the implant of FIG. 1A taken along lines 1D—1D of FIG. 1A;

DETAILED DESCRIPTION OF PREFERRED EMBODIMENTS

Figure 2:
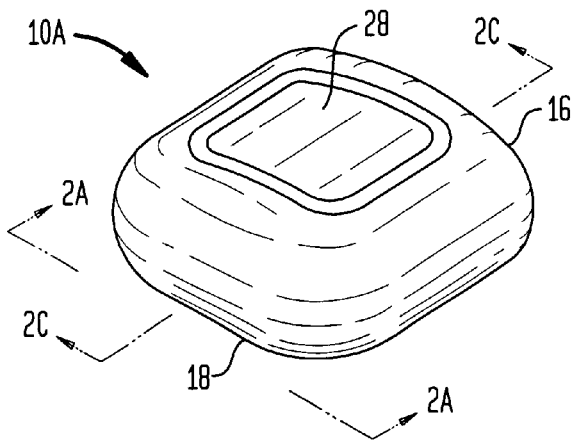
FIG. 2 is a perspective view of the present invention in the form of a femoral ring implant.
Figure 2A:
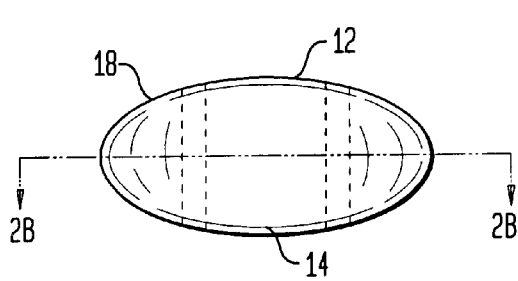
FIG. 2A is a plan view of the posterior end of the implant of FIG. 2 taken along lines 2A—2A.
Figure 2B:
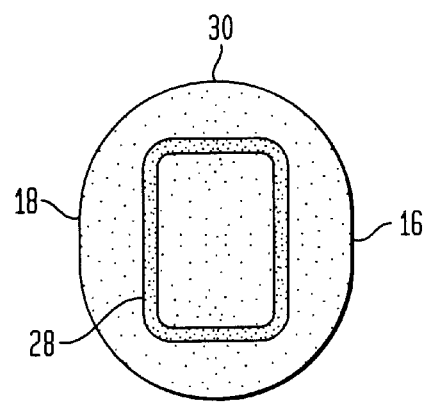
FIG. 2B is a cross-sectional view of the implant of FIG. 2 taken along lines 2B—2B in FIG. 2A.
Figure 2C:
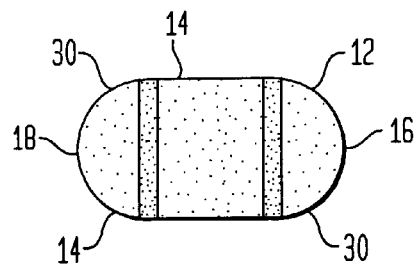
FIG. 2C is a cross sectional view of the implant of FIG. 2 taken along lines 2C—2C in FIG. 2.

The artificial bone graft implant of the present invention has two basic portions, each composed of a biocompatible microporous material. A first portion is a core element and a second portion is a shell element that partially surrounds, and is bonded with, the core element through an interface region. The core is formed of a highly porous composition which allows for bone ingrowth and the shell is formed of a low porosity dense composition which provides for mechanical strength. This results in the average pore size of the core being greater than the average pore size of the shell. Also, the percent porosity of the core will be greater that the percent porosity of the shell. The interface region connecting the two portions may have gradient pore sizes in which the gradient range goes from a large pore size adjacent the core element to a small pore size adjacent the shell element. The core element can be formed in any shape but in one preferred embodiment it is formed of two uniformly sized cores generally oblong in shape and spaced apart from each other. A second preferred embodiment has one core element generally rectangular in shape.

The shell element can also have a porous coating on its outer surface to promote bone ingrowth over all or a portion of the shell element in addition to the highly porous core element. Alternatively, the shell element can be formed with a gradient of pore sizes rather than being formed of a unitary low porosity dense composition. In this embodiment, a center portion of the shell element is of a dense or low porosity which gradually changes to a high porosity outside surface. The core element remains the same in this alternative embodiment.

The inventive implant is made from a microporous material that, after surgical implantation, bonds to the natural bone of the patient to form a rigid structure. Such material encompasses, but is not limited to, biocompatible metalics, ceramics (including hydroxylapatite), polymers, and composite materials consisting of phosphate(s), bioactive glass (es), and bioresorbable polymer(s). The implant is preferably made from a ceramic, most preferably a hydroxylapatite such as calcium hydroxylapatite, having a chemical formula $Ca_{10}(PO_4)_6(OH)_2$, available from Smith & Nephew Richards, Inc, 1450 Brooks Road, Memphis, Tenn. 33116 U.S.A. The use of such materials in implants is known in the art, see for example U.S. Pat. No. 4,863,476, whose disclosure is incorporated in its entirety by reference herein.

The dense portion of the preferred hydroxylapatite implant can be formed by pressing the dry HAp powder which is followed by sintering. The amount of pressure required for the pressing is dictated by the shape of the implant, but is typically in the range of 1000 to 2000 psi (6.9 to 14.8 MPa). The pressure is used to consolidate the powder and maximize packing. The optimal sintering protocol is dependent on the size and shape of the green (unsintered) part. The sintering could, but does not necessarily, include simultaneous use of heat and isostatic pressure (HIP). Sintering atmospheres can include argon, nitrogen, air and vacuum. The porous portion of the preferred hydroxylapatite implant involves the addition of bubbling agents, such as hydrogen peroxide, to a HAp slurry. The slurry is then dried and sintered.

The hybrid dense/high porosity structure of the inventive implant can be produced by a two-step process wherein the dense and highly porous portions are produced separately (as described above) then combined with the interface and sintered to produce the final hybrid implant.

Alternatively, the hybrid dense/highly porous implant can be produced in a one-step process by injection molding a HAp slurry containing a binder that will burn out during sintering which will create the different porosity of the core and shell.

In an alternative embodiment, the inventive implant can be formed of a unitary structure having a gradient of pore sizes. The preferred gradient consists of a dense or low porosity center which gradually changes to a high porosity outside surface. The average pore size of the highly porous region would range from 100 to 800 microns. Bone requires a minimum pore size before ingrowth can occur. The maximum size would be limited by the strength requirements of the implant. The percent porosity at which the implant structure is considered to have high porosity is generally between about 30% porosity (or 70% dense) to 40% porosity (or 60% dense) which would still allow the implant to maintain the required mechanical strength. However, the maximum amount of percent porosity would most likely need to be lower than 40% in order to maintain adequate strength of the implant structure.

The artificial bone graft implant of the present invention can be formed in any desirable shape for use in surgical procedures requiring a bone graft implant, such as facial reconstruction, the repair of long bone defects, and spinal surgery. For example, in spinal surgery, bone graft implants are frequently used when a fusion is done as part of an intervertebral discectomy procedure. During the fusion procedure, the bone graft implant is inserted into the intervertebral space after the disc is removed.

An embodiment of the present invention as an artificial spinal disc implant 10 is illustrated in FIGS. 1, 1A–D. As shown, implant 10 has two opposed lateral surfaces 12, 14 with an anterior end 16 that tapers toward a posterior end 18. The implant includes a pair of high porosity inner cores or inserts 20, 22 that extend between the opposed lateral surfaces 12, 14, a low porosity dense shell 24 surrounding the cores 20, 22, and a region of gradient porosity 26 can separate the cores 20, 22 and shell 24. The cores 20, 22 are generally oblong in shape with curved end portions and are generally spaced equal-distant apart from each other and the outer surface of the opposed lateral surfaces 12, 14.

A second embodiment of the invention as a femoral ring implant 10A, is illustrated in FIGS. 2, 2A–2C. Implant 10A has one central porous core 28 extending between the opposed lateral surfaces 12, 14 and a dense shell 30. The central core 28 can be separated from the dense shell 30 by a region of gradient porosity 32. The central core 28 is generally rectangular in shape but could also be generally oval in shape. The femoral ring implant 10A can be used to repair long bones or it can be used as a spinal disc replacement such as implant 10.

Figure 3:
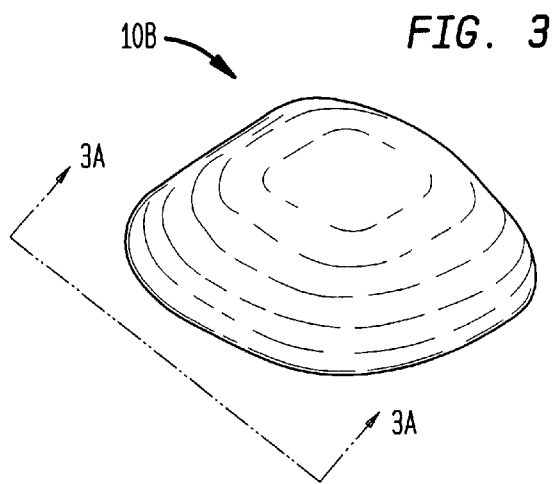
FIG. 3 is a perspective view of the present invention in the form of an alternate spinal disc implant.
Figure 3A:
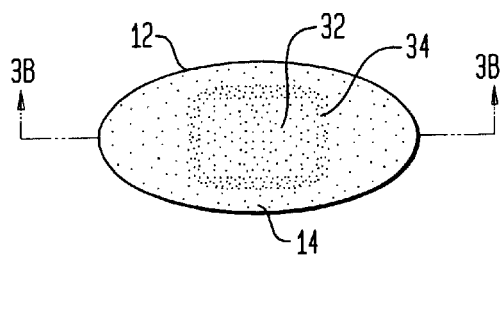
FIG. 3A is a plan view of the posterior end of the implant of FIG. 3 taken along lines 3A—3A in FIG. 3.
Figure 3B:
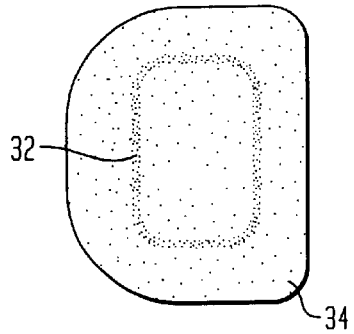
FIG. 3B is a cross-sectional view of the implant of FIG. 3 taken along the lines 3B—3B if FIG. 3A.

The inventive implant formed of a unitary structure having a gradient of pore sizes is illustrated in FIGS. 3, 3A, 3B as implant 10B. Implant 10B has a dense or low porosity center 32 between the opposed lateral surfaces 12, 14 which gradually changes to a high porosity outer portion 34, as shown in FIG. 3B.

Figure 4:
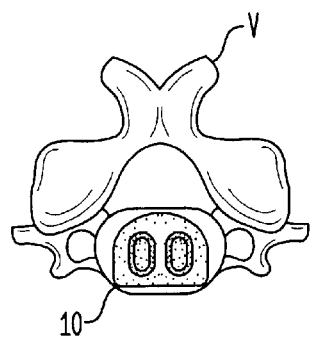
FIG. 4 is a schematic top plan view of a human cervical vertebra with an implanted spinal disk implant of FIG. 1 indicated in solid lines.

The implant 10 is illustrated in FIG. 4 as it would appear when implanted between two cervical spinal vertebrae V (with only one vertebrae being shown) as a replacement for a spinal disc.

In the preferred embodiment of the artificial bone graft implant, the implant is formed of HAp including the core, shell, and gradient regions. The implant may also be made of calcium phosphate or other microporous ceramics, polymers and composite materials. The dense HAp element has a mechanical strength sufficient to bear the loads normally experienced by natural bones, and a compressive strength similar to the natural bones of the body. The porous HAp core element allows for natural bone ingrowth which facilitates permanent fixation of the implant after implantation in natural bone.

Although particular embodiments of the invention have been described in detail for purposes of illustration, various modifications may be made without departing from the spirit and scope of the invention. Accordingly, the invention is not to be limited except as by the appended claims.

What is claimed is:

1. An artificial bone graft implant for use as a replacement for living bone material in surgical procedures requiring the use of bone graft material, the implant comprising:

a) a body formed of a biocompatible microporous material adapted to bond to bone, the body configured to be implanted into a prepared site in a patient's bone tissue, the body having a center portion, an outer portion and a pair of opposed outer surfaces defining the body;

b) the biocompatible microporous material having a relatively low average porosity in the center portion that gradually changes to a relatively high average porosity in the outer portion;

c) wherein the pore size of the center portion of the body allows for a load bearing capacity similar to natural bone and the pore size of the outer portion of the body allows for the ingrowth of bone tissue, the biocompatible microporous material being a calcium phosphate.

2. An artificial bone graft implant for use as a replacement for living bone material in surgical procedures requiring the use of bone graft material, the implant comprising:

a) a body formed of a biocompatible microporous material adapted to bond to bone, the body configured to be implanted into a prepared site in a patient's bone tissue, the body having a center portion, an outer portion and a pair of opposed outer surfaces defining the body;

b) the biocompatible microporous material having a relatively low average porosity in the center portion that gradually changes to a relatively high average porosity in the outer portion;

c) wherein the pore size of the center portion of the body allows for a load bearing capacity similar to natural bone and the pore size of the outer portion of the body allows for the ingrowth of bone tissue, the biocompatible microporous material being hydroxylapatite.

3. An implant for replacing the supporting function of an intervertebral space defined between adjacent vertebrae, comprising a prosthetic implant member dimensioned for insertion within a space provided by at least partial removal of the intervertebral disc, the implant member including a first implant portion and a second implant portion, the first implant portion comprising a microporous material formed to define a predetermined configuration and having a first relatively high average porosity to facilitate rapid bone ingrowth within the first implant portion, the second implant portion comprising a microporous material formed to define a predetermined configuration and having a second relatively low average porosity to support and maintain the adjacent vertebrae in spaced relation during permanent fixation of the implant member within the adjacent vertebrae, the first implant portion being disposed in a peripheral area of the implant member and the second implant portion being disposed in a central area of the implant member, the microporous material being selected from the group consisting of calcium phosphate, bioactive glass, bioresorbable polymers, and hydroxylapatite.

4. The implant of claim 3 wherein the microporous material is a hydroxylapatite.

5. The implant of claim 3 including an intermediate implant portion between the first and second implant portions, the intermediate implant portion comprising a microporous material having an average porosity ranging between the first porosity of the first implant portion and the second porosity of the second implant portion.

6. The implant of claim 5 wherein the average porosity of the intermediate implant portion gradually increases from a location adjacent the first implant portion to a location adjacent the second implant portion.

7. The implant of claim 3 wherein the implant member includes upper and lower surfaces for respectively engaging upper and lower vertebral portions and defines a height therebetween sufficient to span the intervertebral space and maintain the upper and lower vertebral portions in predetermined spaced relation.

8. The implant of claim 3 wherein the second porosity of the second implant portion is less than about 40%.

* * * * *

UNITED STATES PATENT AND TRADEMARK OFFICE
CERTIFICATE OF CORRECTION

PATENT NO. : 6,607,557 B1
DATED : August 19, 2003
INVENTOR(S) : Robert Brosnahan, Laura Small and Julie A. Bearcroft It is certified that error appears in the above-identified patent and that said Letters Patent is hereby corrected as shown below:

<u>Title page,</u>
Item [75], Inventors, "Laura A. Small" should read -- Laura Small --.

<u>Column 3,</u>
Line 28, "cross sectional" should read -- cross-sectional --.
Line 29, "FIG. 1" should read -- FIG. 1A --.

<u>Column 6,</u>
Line 32, delete "microporous."

Signed and Sealed this

Twenty-seventh Day of January, 2004

JON W. DUDAS
*Acting Director of the United States Patent and Trademark Office*